United States Patent
Richter et al.

(10) Patent No.: US 10,401,330 B2
(45) Date of Patent: Sep. 3, 2019

(54) GAS CHROMATOGRAPH AND MULTIPORT VALVE UNIT FOR A GAS CHROMATOGRAPH

(71) Applicant: Siemens Aktiengesellschaft, Munich (DE)

(72) Inventors: Josef Richter, Karlsruhe (DE); Piotr Strauch, Ruelzheim (DE)

(73) Assignee: Siemens Aktiengesellschaft, Munich (DE)

( * ) Notice: Subject to any disclaimer, the term of this patent is extended or adjusted under 35 U.S.C. 154(b) by 246 days.

(21) Appl. No.: 15/537,144

(22) PCT Filed: Dec. 2, 2015

(86) PCT No.: PCT/EP2015/078310
§ 371 (c)(1),
(2) Date: Jun. 16, 2017

(87) PCT Pub. No.: WO2016/096423
PCT Pub. Date: Jun. 23, 2016

(65) Prior Publication Data
US 2018/0003681 A1     Jan. 4, 2018

(30) Foreign Application Priority Data
Dec. 18, 2014 (DE) .................. 10 2014 226 481

(51) Int. Cl.
*G01N 30/20*     (2006.01)
*F16K 11/02*     (2006.01)
(Continued)

(52) U.S. Cl.
CPC ............ *G01N 30/20* (2013.01); *F16K 11/022* (2013.01); *G01N 30/40* (2013.01); *G01N 30/468* (2013.01);
(Continued)

(58) Field of Classification Search
CPC ...... G01N 30/20; G01N 30/40; G01N 30/468; G01N 2030/025; G01N 2030/201; G01N 2030/205; G01N 2030/402; F16K 11/022
See application file for complete search history.

(56) References Cited

U.S. PATENT DOCUMENTS 3,071,005 A * 1/1963 Skidmore .............. G01N 30/20
    222/308
3,411,525 A * 11/1968 Auger ....................... F16K 3/08
    137/270
(Continued)

FOREIGN PATENT DOCUMENTS

| | | |
|---|---|---|
| AU | 1386976 A | 11/1977 |
| CN | 1323380 | 11/2001 |

(Continued)

OTHER PUBLICATIONS

Office Action dated Mar. 16, 2018 which issued in the corresponding Chinese Patent Application No. 201580068759.6.

*Primary Examiner* — David J Bolduc
(74) *Attorney, Agent, or Firm* — Cozen O'Connor

(57) ABSTRACT

A gas chromatograph that includes a metering chamber, two separating devices and a multiport valve unit having switching functions for metering, straight separation, cutting and backflush, where the multiport valve unit is formed as a multiport diaphragm valve.

9 Claims, 4 Drawing Sheets

(51) Int. Cl.
*G01N 30/40* (2006.01)
*G01N 30/46* (2006.01)
*G01N 30/02* (2006.01)

(52) U.S. Cl.
CPC . *G01N 2030/025* (2013.01); *G01N 2030/201* (2013.01); *G01N 2030/205* (2013.01); *G01N 2030/402* (2013.01)

(56) References Cited

U.S. PATENT DOCUMENTS

| | | | |
|---|---|---|---|
| 4,006,753 A * | 2/1977 | Ingram, Jr. | F16K 7/16 137/607 |
| 4,007,626 A * | 2/1977 | Roof | G01N 30/12 73/19.02 |
| 4,848,722 A | 7/1989 | Webster | |
| 4,852,851 A | 8/1989 | Webster | |
| 4,923,616 A * | 5/1990 | Hirata | B01D 15/1828 210/676 |
| 5,132,012 A * | 7/1992 | Miura | G01N 30/6095 210/198.2 |
| 5,392,634 A * | 2/1995 | Asano | G01N 30/40 422/89 |
| 6,453,725 B1 | 9/2002 | Dahlgren et al. | |
| 2002/0062870 A1 | 5/2002 | Xu et al. | |
| 2002/0131905 A1 | 9/2002 | Cordill | |
| 2004/0014227 A1 * | 1/2004 | Frederick | G01N 30/20 436/43 |
| 2004/0234414 A1 | 11/2004 | Bezzola | |
| 2005/0218055 A1 * | 10/2005 | Hayashi | G01N 30/463 210/198.2 |
| 2006/0185419 A1 | 8/2006 | Gamache et al. | |
| 2008/0044309 A1 * | 2/2008 | Yamashita | G01N 30/08 422/52 |
| 2008/0052013 A1 | 2/2008 | Bailey et al. | |
| 2008/0053543 A1 * | 3/2008 | Baier | G01N 30/20 137/625.15 |
| 2008/0053901 A1 * | 3/2008 | Mierendorf | B01D 15/1842 210/635 |
| 2008/0093300 A1 * | 4/2008 | Clarke | B01D 15/1864 210/656 |
| 2009/0014078 A1 * | 1/2009 | Gamache | F16K 7/12 137/625.48 |
| 2009/0152481 A1 * | 6/2009 | Gamache | F16K 11/20 251/12 |
| 2010/0000301 A1 * | 1/2010 | Iwata | G01N 30/463 73/61.55 |
| 2010/0154511 A1 * | 6/2010 | Lambertus | G01N 30/463 73/25.03 |
| 2011/0290001 A1 | 12/2011 | Strauch | |
| 2012/0096932 A1 * | 4/2012 | Anderson, Jr. | G01N 30/20 73/61.53 |
| 2012/0125440 A1 * | 5/2012 | Price | F16K 11/074 137/1 |
| 2013/0283336 A1 | 10/2013 | Macy et al. | |
| 2014/0178979 A1 * | 6/2014 | Herman | G01N 30/08 435/288.6 |
| 2014/0208827 A1 * | 7/2014 | Bailey | G01N 30/32 73/23.42 |
| 2014/0298990 A1 * | 10/2014 | Fan | G01N 30/463 95/23 |
| 2015/0204828 A1 * | 7/2015 | Witt | G01N 30/20 204/601 |
| 2015/0338382 A1 * | 11/2015 | Guan | G01N 30/28 73/23.42 |
| 2017/0010243 A1 * | 1/2017 | Gaita | G01N 30/78 |
| 2017/0321813 A1 * | 11/2017 | Olovsson | F16K 11/0743 |

FOREIGN PATENT DOCUMENTS

| | | |
|---|---|---|
| CN | 102980962 | 3/2013 |
| DE | 3853592 T2 | 11/1995 |
| EP | 0400016 B1 | 4/1995 |
| WO | WO 2007/028130 A2 | 3/2007 |
| WO | WO 2010/066571 A1 | 6/2010 |

* cited by examiner

GAS CHROMATOGRAPH AND MULTIPORT VALVE UNIT FOR A GAS CHROMATOGRAPH

CROSS-REFERENCE TO RELATED APPLICATIONS

This is a U.S. national stage of application No. PCT/EP2015/078310 filed 2 Dec. 2015. This application claims the priority of German application no. DE 102014226481.2 filed Dec. 18, 2014, the content of which is incorporated by reference in its entirety.

BACKGROUND OF THE INVENTION

1. Field of the Invention

The invention relates to a gas chromatograph and a multiport valve unit for a gas chromatograph.

2. Description of the Related Art

U.S. Pat. No. 6,453,725 B1 discloses a gas chromatograph with a multiport valve unit that serves sample dosing and switching between two chromatographic separating devices with downstream detectors. The multiport valve unit comprises ten controllable valves, which are connected in series and are open or closed depending on their activation. In each case, immediately adjacent valves of the series circuit are activated here in a different manner, so that the multiport valve unit has two different switching positions, in which each second valve is either closed or open.

At the start and end of the series circuit and at the different points of connection of the adjacent valves, a sample feed, a sample vent, an inlet and an outlet of a metering chamber, a first separating device with a subordinate first detector, a second separating device with a subordinate second detector and a gas outlet are connected such that, in a first switching position of the multiport valve unit, a sample taken from a technical process is conveyed in a continuous stream through the metering chamber, while at the same time the first separating device with the first detector are backflushed and parallel thereto the second separating device with the second detector are forward-flushed with a carrier gas. In a second switching position of the multiport valve unit, the sample quantity contained in the metering chamber is guided successively through the first and the second separating device via the carrier gas and here broken down here into different sample components, which are detected with the detectors. At the same time the sample stream is guided past the metering chamber.

US 2002/0131905 A1 discloses a modification of the previously described multiport valve unit which, between the first switching position, in which the sample is conveyed through the metering chamber, and the second switching position, in which the sample is conveyed out of the metering chamber into a separating device, adopts a further switching position, in which the metering chamber is briefly separated from the sample feed, in order to enable matching of the pressure in the metering chamber to the outside pressure.

The multiport valve unit of the conventional gas chromatograph has an upper part, a lower part and a central part in the form of a disk, which upon interpositioning of a first diaphragm is connected to the upper part and upon interpositioning of a second diaphragm is connected to the lower part. The upper part contains five recesses in its body surface abutting the first diaphragm, into which control air can be introduced via a first control line. The lower part contains five further recesses in its body surface abutting the second diaphragm, into which the control air can be introduced via a second control line. The central part contains in each case a pair of holes on its top abutting the first diaphragm and on its underside abutting the second diaphragm, in the areas opposite the ten recesses, where each pair of holes forms fluid ports in each case of one of the ten valves. Upon introduction of control air into the five recesses of the upper part, the first diaphragm closes the respectively opposite holes in the central part and the five valves are closed. At the same time, in the absence of control air in the further five recesses of the lower part, the second diaphragm recedes into the further five recesses as the holes opposite it are released, and the further five valves are open. The control air is introduced alternately into the five recesses of the upper part and the further five recesses of the lower part, so that the five valves and the further five valves open and close alternately. Formed in the central part are fluid channels, which connect holes on the top of the central part to holes on the underside and thus switch the five valves and the further five valves alternately in series. The fluid channels further lead to external ports, which are mounted on the central part, and serve to attach the different components of the gas chromatograph to the multiport valve unit.

Because of the dead volumes of the fluid channels in the central part of the known multiport valve unit, its use in certain applications may be limited. Thus, as already mentioned above, in the first switching position of the multiport valve unit, the sample taken from the technical process is guided through the metering chamber via one of the ten valves and in the second switching position transferred from the metering chamber into the chromatographic separating devices via a different valve via the carrier gas. At the point of switching, a part of the fluid channel between the valves involved forming the dead volume is filled with the sample, which then diffuses from the dead volume into the carrier gas, which leads to an imprecise injection of the sample into the carrier gas stream, connected with a reduction in the resolution of the subsequent chromatographic separation.

WO 2007/028130 A2 shows a very similar gas chromatograph that likewise has a multiport valve unit comprising ten controllable valves connected in series, which serves sample dosing and switching between two chromatographic separating devices. Here, immediately adjacent valves of the series circuit in each case are also differently activated, so that the multiport valve unit has two different switching positions, in which each second valve is either closed or open. In contrast to the conventional gas chromatograph shown in U.S. Pat. No. 6,453,725 B1, in the first switching position of the multiport valve unit both separating devices are backflushed with the carrier gas.

The multiport valve unit also differs in its structure from that known from U.S. Pat. No. 6,453,725 B1, as it has only one diaphragm and all ten recesses serving to introduce the control air are jointly formed in one component, which abuts one of the sides of the diaphragm with its body surface containing the recesses. Accordingly the pairs of holes that form the fluid ports of the individual valves are also formed together in a further component, which abuts the other side of the diaphragm with its side containing the pairs of holes. In the further component, fluid channels are formed in a V-shaped arrangement, which connect the respectively adjacent pairs of holes and thus switch the ten valves in series. The fluid channels further lead to external ports, which serve to attach the different components of the gas chromatograph to the multiport valve unit. Here, the limitations or problems explained above in relation to the injection of the sample into the carrier gas stream as a result of the dead volumes of the fluid channels also arise.

EP 0 400 016 B1 discloses a multiport valve unit with a lower part in the form of a disk, in which in each case a recess is formed in an outer surface for each valve, into which control air can be introduced via an individual control line. A diaphragm abuts the outer surface of the lower part with the recesses. The recesses can also be formed in an upper part or intermediate part in the form of a disk, which abuts the diaphragm on the opposite side. In the case of the intermediate part, this contains pairs of holes opening into the recesses, where each pair of holes forms fluid ports in each of the valves. On its side facing away from the diaphragm, the intermediate part contains grooves, which are covered by an overlying upper part and which connect the fluid ports connected in series to each other and/or lead from the fluid ports to prescribed locations, to which they are connected with external ports via drilled holes in the upper part.

In order to achieve precise sample dosing in a gas chromatograph, it is, for example, known from WO 2010/066571 A1 to convey the sample amount directed from the metering chamber by the carrier gas to an injector operating without valves, which diverts part of this sample amount and introduces it into the separating devices as a precisely delimited sample plug. A switching device likewise operating without valves is further provided between the first separating device with the downstream first detector and the second separating device with the downstream second detector, in order to convey sample components that are not sufficiently separated at the end of the first separating device into the second separating device, and keep sample components that are already sufficiently separated at the end of the first separating device and have been detected away from the second separating device. The controlling of the injector and the switching device occurs via pressure differences in gas paths, which necessitates precise pressure regulation and adjustment of the pressure drops via flow resistances. In addition, the switching device requires an auxiliary gas supply, which is connected to correspondingly high carrier gas consumption.

SUMMARY OF THE INVENTION

It is an object of the invention to enable sample dosing and separation column switching via a multiport valve unit in a gas chromatograph.

This and other objects and advantages are achieved in accordance with the invention by a gas chromatograph and a multiport valve unit for the gas chromatograph.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further illustration of the invention and its advantages reference is made below to the figures of the drawing, in which:

FIGS. 1 through 4 each show in an exemplary schematic representation a circuit diagram of a gas chromatograph with a sample feed 1 and a sample vent 2, a metering chamber 3 in the form of an injection loop with an inlet 4 and an outlet 5, a carrier gas feed 6, a first separating device 7 with a downstream first detector 8, a second separating device 9 with a downstream second detector 10, a first, second and third gas outlet 11, 12, 13, and a multiport valve unit 14 comprising a first valve 15, a second valve 16, a third valve 17, a fourth valve 18 and a fifth valve 19 in a first series circuit 20, a sixth valve 21 and a seventh valve 22 in a second series circuit 23 and a eighth valve 24, a ninth valve 25 and a tenth valve 26 in a third series circuit 27.

Figure 1:
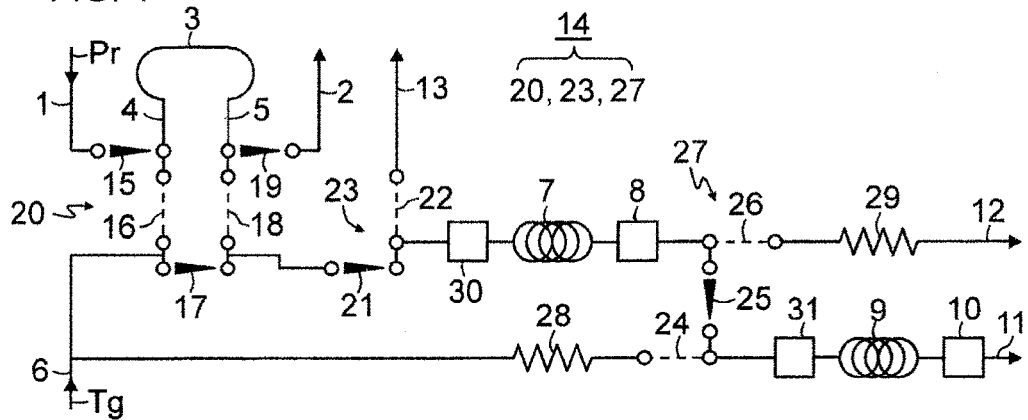
FIGS. 1 through 4 show an exemplary embodiment of the inventive gas chromatograph with a multiport valve unit comprising ten valves in four different switching positions.

The sample feed 1 is attached to the start and the sample vent 2 is attached to the end of the first series circuit 20. The inlet 4 of the metering chamber 3 is attached to the connection between the first and second valve 15, 16 and the outlet 5 of the metering chamber 3 is attached to the connection between the fourth and fifth valve 18, 19. The carrier gas feed 6 is attached to the connection between the second and third valve 16, 17 and further connected to the start of the third series circuit 27 via a flow resistance 28. The end of the third series circuit 27 is connected to the second gas outlet 12 via a further flow resistance 29. The start of the second series circuit 23 is attached to the connection between the third and fourth valve 17, 18 and the end of the second series circuit 23 is attached to the third gas outlet 13. The first separating device 7 with the first detector 8 is arranged between the connection between the sixth and seventh valve 21, 22 and the connection between the ninth and tenth valve 25, 26. The second separating device 9 with the second detector 10 is arranged between the connection of the eighth and ninth valves 24, 25 and the first gas outlet 11.

An additional detector 30, 31 is in each case installed immediately upstream of the first separating device 7 and the second separating device 9. The detectors 8, 10, 30, 31 preferably take the form of thermal conductivity detectors, which respond to substances with different thermal conductivity to the carrier gas used, and thus detect in a non-destructive manner.

The valves 15, 16, 17, 18, 19, 21, 22 are activated or capable of being activated such that, within the first series circuit 20 and within the second series circuit 23, each second valve is either closed or open. This means that in the case of closed valves 15, 17, 19 of the first series circuit 20, the valves 16, 18 are open (and vice versa) and that in the case of a closed valve 21 of the second series circuit 23, the valve 22 is open (and vice versa). The valves 24, 25, 26 of the third series circuit 27 can, on the other hand, be activated independently of each other.

FIG. 1 shows the gas chromatograph with the multiport valve unit 14 in a first switching position, in which the valves 15, 17, 19, 21, 25 are open and the remaining valves 16, 18, 22, 24, 26 are closed. In this first switching position, sample Pr taken from a technical process is passed through the metering chamber 3 in a continuous stream via the sample feed 1 and then disposed of via the sample vent 2 or returned back to the process. At the same time, the first separating device 7 and the associated detectors 8, 30 and then the second separating device 9 and the associated detectors 10, 31 are flushed with a carrier gas Tg, which is supplied via the carrier gas feed 6 and disposed of via the first gas outlet 11.

Figure 2:
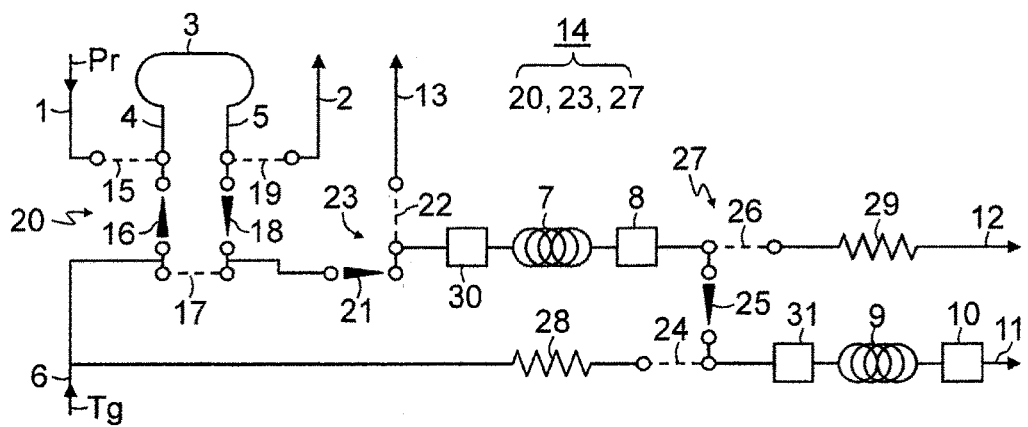

To inject a prescribed sample amount from the metering chamber 3 into the carrier gas stream the multiport valve unit 14 is briefly switched into a second switching position as shown in FIG. 2 through switching of the valves 15, 16, 17, 18, 19 of the first series circuit 20. For the brief duration of this second switching position, in which the valves 16, 18, 21, 25 are open and the valves 15, 17, 19, 22, 24, 26 closed, the carrier gas Tg is diverted into the injection loop 3 and forces the sample amount contained therein in the form of a sample plug through the open valve 18 in the direction of the first separating device 7. Through timely control of the valves 15, 16, 17, 18, 19 of series circuit 20, the dosed sample amount can be reduced to a precisely delimited sample plug which can be as short as required.

Fluid connections are always present between the valves 15, 16, 17, 18, 19 of the first series circuit 20 and also between the valves of the other series circuits 23, 27, which for structural reasons cannot be as short as may be desired. These form dead spaces upon switching of the valves lying respectively upstream and downstream of them. In order to avoid the fluid connections between the first and second valve 15, 16 and between the fourth and fifth valve 18, 19 having the sample Pr flow through them in the first switching position (FIG. 1) of the multiport valve unit 14, so that in the second switching position (FIG. 2) the sample diffuses from the fluid connections now forming dead spaces into the carrier gas stream and thus results in an imprecise injection of the sample into the carrier gas stream, the inlet 4 and outlet 5 of the metering chamber 3 are in each case attached asymmetrically to the connections between the first and second valve 15, 16 or the fourth and fifth valve 18, 19 respectively. This means that the inlet 4 of the metering chamber 3 lies as close as possible to the first valve 15 and the outlet 5 of the metering chamber 3 as close as possible to the fifth valve 19.

To terminate the sample dosing in the carrier gas stream, the valves 15, 16, 17, 18, 19 of the first series circuit 20 are once again switched, so that the multiport valve unit 14 again assumes the first switching position (FIG. 1). While the sample Pr emanating from the technical process again flows continuously through the metering chamber 3, the carrier gas Tg now conveys the sample plug taken from the metering chamber 3 through the first separating device 7, where the sample is broken down into different sample components, which appear in succession at the output of the first separating device 7 and are detected there with the detector 8. Sample components with a low boiling point (low boilers, such as nitrogen, carbon monoxide, hydrogen sulfide, carbon dioxide, or ethane), which on account of their short retention times in the first separating device 7 appear first and are thus insufficiently separated from each other, are conveyed through the open valve 25 into the second separating device 9, where they are further separated and subsequently detected with the detector 10. The second separating device 9 is accordingly designed in particular for low boilers and the first separating device 7 for high boilers (e.g., propane, butane and higher hydrocarbons).

Figure 3:
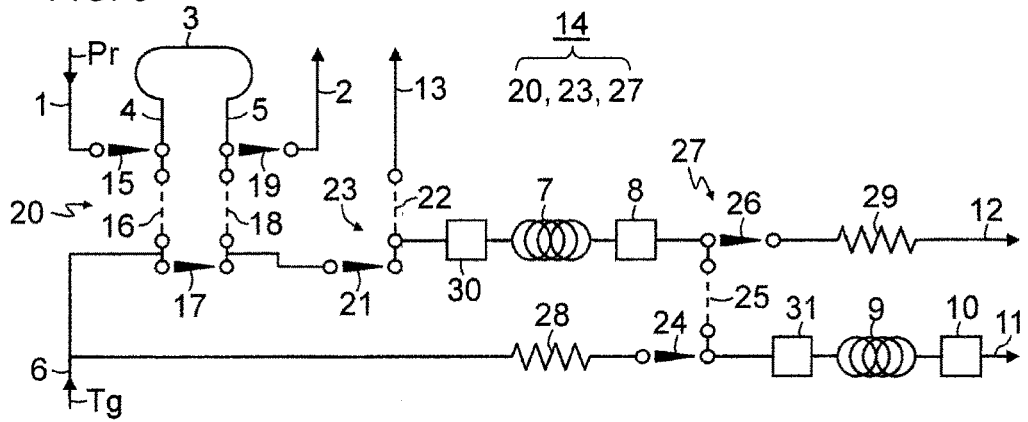

As, on the one hand, high boilers are already sufficiently separated in the first separating device 7 and, on the other hand, their throughput time in the second separating device 9 designed for low boilers would be very long or they could damage the second separating device 9, they must be kept away from the second separating device 9. To this end, the multiport valve unit 14 is switched to a third switching position shown in FIG. 3 by switching the valves 24, 25, 26 of the third series circuit 27, as soon as the low boilers to be further separated in the second separating device 9 have passed valve 25 or before the first of the high boilers to be separated and then detected in the first separating device 7 reaches the valve 25. In this third switching position, the valves 15, 17, 19, 21, 24, 26 are open and the valves 16, 18, 22, 25 closed. A partial stream of the carrier gas Tg now passes via the flow resistance 28 and through the open valve 24 into the second separating device 9, in order to convey the low boilers through the second separating device 9 without interruption. The other partial stream of the carrier gas Tg continues to convey the high boilers through the first separating device 7 and after their detection in the detector 8 through the open valve 26 and via the further flow resistance 29 to the second gas outlet 12.

Figure 4:
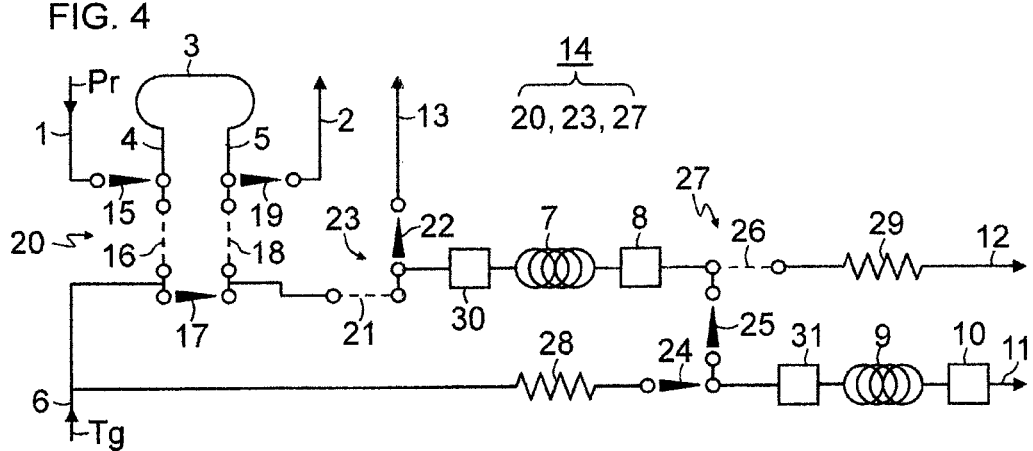

After a predefined high boiler (e.g., n-pentane) has been detected at the output of the first separating device 7 by the detector 8, the multiport valve unit 14 can be switched to a fourth switching position (as shown in FIG. 4) by switching the valves 21, 22 of the second series circuit 23 and by switching the valves 25, 26 of the third series circuit 27. In this fourth switching position, the valves 15, 17, 19, 22, 24, 25 are open and the valves 16, 18, 21, 26 closed. The carrier gas Tg flowing via the flow resistance 28 and through the open valve 24 continues to convey the low boilers through the second separating device 9 and additionally through the open valve 24 the high boilers (e.g., hexane and higher hydrocarbons) remaining in the first separating device 7 back to the detector 30, where they are detected in total and subsequently disposed of via the third gas outlet 13. By changing the carrier gas pressure, the backflush procedure is slowed down or accelerated, e.g., to raise the detection limit or shorten the duration of the chromatography cycle.

Thereafter, the multiport valve unit 14 is once more switched into the first switching position (as shown in FIG. 1) by switching the valves 15, 16, 17, 18, 19 of the first series circuit 20, the valves 21, 22 of the second series circuit 23 and the valves 24 of the third series circuit 27, so that the first separating device 7 with the associated detectors 8, 30 and the second separating device 9 with the associated detectors 10, 31 are flushed with the carrier gas Tg.

To summarize, in the above-described chromatography cycle, the multiport valve unit 14 successively assumes the following switching positions:
first switching position (FIG. 1),
second switching position (FIG. 2),
first switching position "straight ahead" (FIG. 1),
third switching position "cut" (FIG. 3),
fourth switching position "backflush" (FIG. 4).

It is also possible to make use only of a subset of the above-mentioned switching functions during a chromatography cycle, such as only "straight ahead" and "backflush" without "cut".

The flow resistances 28, 29 serve to pneumatically balance the system in the different switching positions of the multiport valve unit 14. Additionally or alternatively, the separating devices 7, 9, via auxiliary resistances, and/or the carrier gas pressure can also contribute to or be used for the balancing.

Figure 5:
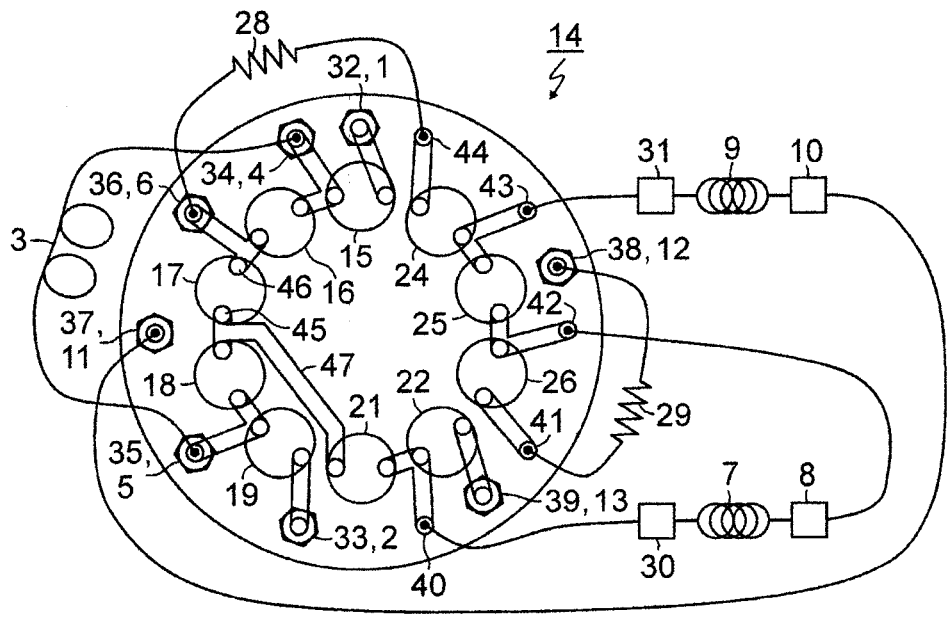
FIG. 5 shows an exemplary multiport valve unit with the different components of the gas chromatograph connected thereto in accordance with the invention.

FIG. 5 shows in a schematic representation an exemplary multiport valve unit 14 with the different components of the gas chromatograph connected thereto. The ten valves 15, 16, 17, 18, 19, 21, 22, 24, 25, 26 are arranged along an inner circle. Arranged around these on an outer circle are external ports 32, 33, 34, 35, 36, 37, 38, 39 for the sample feed 1, the sample vent 2, the inlet 4 and outlet 5 of the metering chamber 3, the carrier gas feed 6 and the gas outlets 11, 12, 13. Further ports 40, 41, 42, 43, 44 serve to attach the first separating device 7 with the associated detector 30 to the valves 21, 22, the flow resistance 29 to the valve 26, the first separating device 7 with the associated detector 8 to the valves 25, 26, the second separating device 9 with the associated detector 31 to the valves 24, 25 and the flow resistance 28 to the valve 24. Each valve, such as 17, has two fluid ports 45, 46, to which it is connected with adjacent valves and/or external ports via fluid lines 47.

Figure 6:
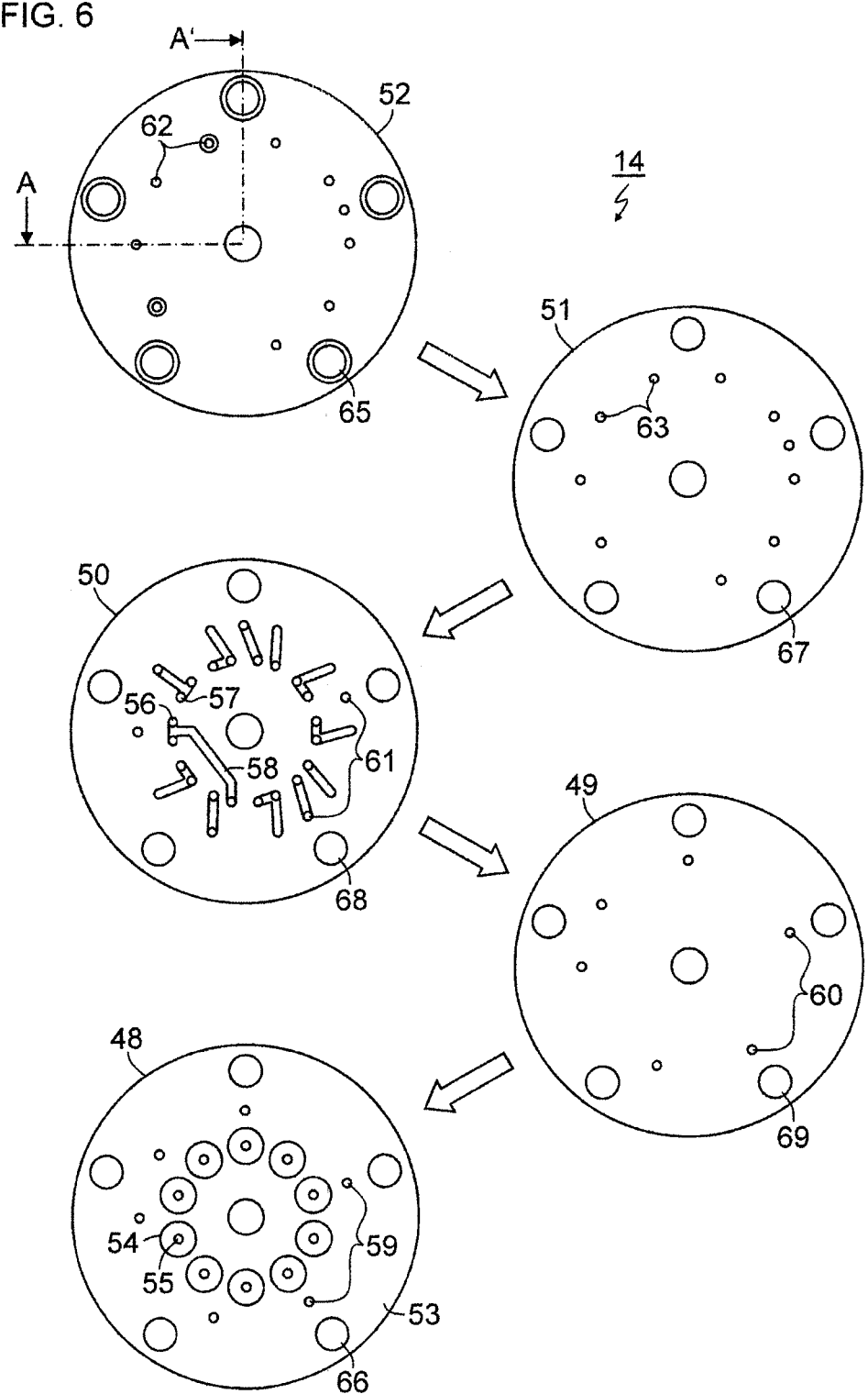
FIG. 6 shows an exemplary top view of individual components of the multiport valve unit in accordance with the invention.
Figure 7:
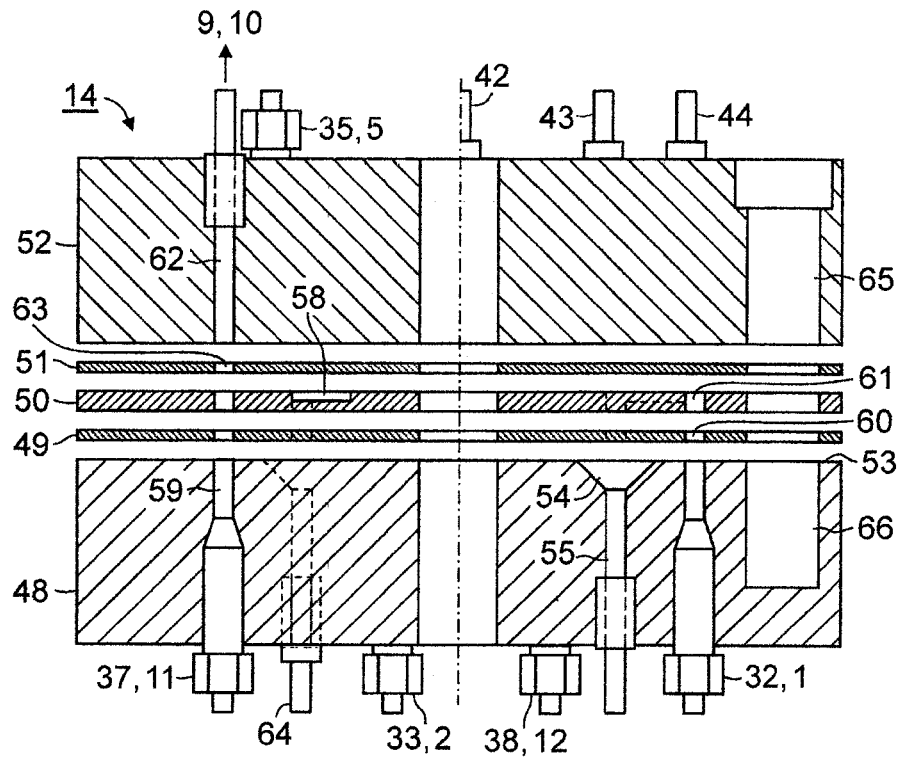
FIG. 7 shows an exemplary sectional representation of the multiport valve unit in accordance with the invention.
Figure 8:
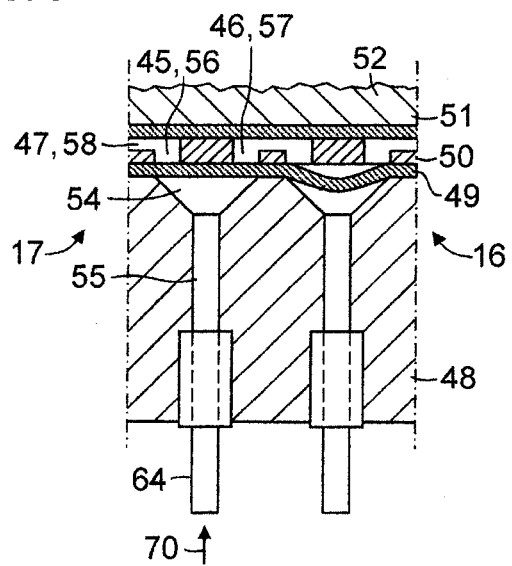
FIG. 8 shows a detailed sectional representation of the multiport valve unit in accordance with the invention.

There follows a more detailed explanation of the structure of the multiport valve unit 14 based on FIGS. 6, 7 and 8. In the exemplary embodiment shown, the multiport valve unit 14 comprises a lower part 48 in the form of a disk, a diaphragm 49, a control disk 50, an optional sealing foil 51 (e.g., polyimide) and an upper part 52 in the form of a disk, which are mounted on each other in this order.

FIG. 6 shows the specified components of the multiport valve unit 14, individually and seen from above.

FIG. 7 shows the multiport valve unit 14 in a section along the line AA' in FIG. 6, where the components are represented separately from each other so that they may be better distinguished.

FIG. 8 shows an individual unit of the multiport valve unit 14 in a section through the valves 16 and 17.

The lower part 48 in the form of a disk contains in an outer surface 53 facing the diaphragm 49 in each case a recess 54 for each of the valves 15, 16, 17, 18, 19, 21, 22, 24, 25, 26, into which control air can be introduced via an individual control line 55. The diaphragm 49 lies between the lower part 48 and the control disk 49, which each contain a pair of holes 56, 57 in the areas opposite the recesses 54, where each pair of holes 56, 57 forms the fluid ports 45, 46 (FIG. 5) in each case of one of the valves 15, 16, 17, 18, 19, 21, 22, 24, 25, 26. On its side facing away from the diaphragm 48, the control disk 49 contains grooves 58, which with an overlaid sealing foil 51 form the fluid lines 47 (FIG. 5), which connect the fluid ports of the valves, in each case connected in series, to each other and lead from selected fluid ports outwards to prescribed positions, from which they are connected to the external ports 32, 33, 34, 35, 36, 39, 40, 41, 42, 43, 44, as will be explained subsequently in greater detail. The external ports 37, 38 forming the gas outlets 11, 12 serve to attach the second separating device 9 and associated detector 10 or respectively the flow resistance 29, and are not connected to fluid lines formed by grooves in the control disk 49.

The external ports 32, 33, 36, 37, 38, 39 for the sample feed 1, the sample vent 2, the carrier gas feed 6 and the gas outlets 11, 12, 13 are mounted on the outer surface of the lower part 48 facing away from the diaphragm 49. Here, the ports 36, 37, 38 are additionally extended through the multiport valve unit 14 as far as the outer surface of the upper part 52 facing away from the diaphragm 49, in order to enable the attachment of the flow resistance 28 there to the carrier gas feed 6, of the second separating device 9 with its associated detector 10 to the gas outlet 11 and of the flow resistance 29 to the gas outlet 12.

The external ports 34, 35 for the inlet 4 and outlet 5 of the metering chamber 3 are mounted on the outer surface of the upper part 52 facing away from the diaphragm 49. The same applies to the ports 40, 41, 42, 43, 44 for attaching the first separating device 7 with associated detector 30 to the valves 21, 22, the flow resistance 29 to the valve 26, the first separating device 7 with the associated detector 8 to the valves 25, 26, the second separating device 9 with the associated detector 31 to the valves 24, 25 and the flow resistance 28 to the valve 24.

The connection between the external ports 32, 33, 34, 35, 36, 39, 40, 41, 42, 43, 44 and the fluid lines 47 and the extension of the ports 36, 37, 38 from the lower part 48 into the upper part 52 and through this takes place via drilled holes 59 in the lower part 48, which align with corresponding holes 60 in the diaphragm 49 and holes 61 in the control disk 48 or via drilled holes 62 in the upper part 52, which align with corresponding holes 63 in the sealing foil 51.

The control lines 55 likewise have external ports 64, which are mounted on the outer surface of the lower part 48 facing away from the diaphragm 49. The upper part 52 and lower part 48 are screwed together, to which end the two parts have mutually aligned drilled holes 65, 66 and the sealing foil 51, control disk 50 and diaphragm 40 contain corresponding openings 67, 68, 69.

Using the example of the valves 16 and 17, FIG. 8 shows the manner in which the multiport valve unit 14 functions. With the introduction of control air 70 into the recess 54 in the lower part 48 belonging to the valve 16, the diaphragm 49 closes the opposite holes 56, 57 (fluid ports 45, 46) in the control disk 50, so that the valve 16 is closed. At the same time, in the absence of control air, the diaphragm 49 in the area of the recess belonging to the valve 17 as the holes opposite it are released, so that the valve 16 is open.

With the fluid lines for the connection of adjacent valves of a series circuit and for the connection of valves with external ports being formed as grooves in a comparatively thin control disk, it is possible to achieve extremely short connection paths with minimal dead volumes, which enable precise sample dosing and switching of separation columns. In addition, solely through the use of different control disks with different fluid line patterns, it is possible to realize different configurations of the multiport valve unit.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas chromatograph comprising:
   a sample feed;
   a sample vent;
   a metering chamber having an inlet and an outlet;
   a carrier gas feed;
   a first separating device having a downstream first detector;

a second separating device having a downstream second detector, a first, second and third gas outlet; and a multiport valve unit comprising a first valve, a second valve, a third valve, a fourth valve and a fifth valve in a first series circuit, a sixth valve and a seventh valve in a second series circuit and an eighth valve, a ninth valve and a tenth valve in a third series circuit;

wherein the sample feed is attached to a start and the sample vent is attached to an end of the first series circuit;

wherein the inlet of the metering chamber is attached to a connection between the first and second valve and the outlet of the metering chamber is attached to a connection between the fourth and fifth valve;

wherein the carrier gas feed is attached to a connection between the second and third valve and to a start of the third series circuit;

wherein an end of the third series circuit is connected to the second gas outlet;

wherein a start of the second series circuit is attached to a connection between the third and fourth valve and an end of the second series circuit is connected to the third gas outlet;

wherein the first separating device having the first detector is arranged between a connection between the sixth and seventh valve and a connection between the ninth and tenth valve; and wherein the second separating device having the second detector is arranged between a connection between the eighth and ninth valve and the first gas outlet.

2. The gas chromatograph as claimed in claim 1, wherein a flow resistance lies between the carrier gas feed and the start of the third series circuit.

3. The gas chromatograph as claimed in claim 1, wherein a further flow resistance lies between the end of the third series circuit and the second gas outlet.

4. The gas chromatograph as claimed in claim 2, wherein a further flow resistance lies between the end of the third series circuit and the second gas outlet.

5. The gas chromatograph as claimed in claim 1, wherein an additional detector is connected immediately upstream of at least one of (i) the first and (ii) the second separating device.

6. The gas chromatograph as claimed in claim 1, wherein the inlet of the metering chamber is connected asymmetrically to the connection between the first and second valve, said inlet being proximate to the first valve; and wherein the outlet of the metering chamber is connected asymmetrically to the connection between the fourth and fifth valve, said outlet being proximate to the fifth valve.

7. A multiport valve unit for a gas chromatograph, comprising:

a plurality of valves, each of said plurality of valves comprising:
a lower part formed as a disk, a recess being formed in an outer surface for each valve of the plurality of valves, into which control air is introducible via an individual control line;
a diaphragm, which on one side abuts the outer surface of the lower part containing a respective recesses;
a control disk, which abuts another side of the diaphragm; and
a pairs of holes in areas opposite the each of the respective recesses, each pair of holes forming fluid ports in each valve of the plurality of valves;

grooves on its side facing away from the diaphragm, which one of (i) connect the fluid ports of valves of the plurality of valves connected in series to each other and (ii) lead from selected fluid ports to prescribed locations;

an upper part formed as a disk, which immediately or with interposition of a sealing foil, abuts a side of the control disk containing the grooves; and external ports, which are mounted on outer surfaces of at least one of (i) the upper part and (ii) the lower part facing away from the diaphragm and which are connected to the grooves and via these to the fluid ports via drilled holes leading to the prescribed locations and extending vertically to the outer surfaces.

8. The multiport valve unit as claimed in claim 7, wherein the recesses are arranged equidistantly along an inner circle and the external ports are arranged along an outer circle.

9. A gas chromatograph comprising:

a sample feed;
a sample vent;
a metering chamber having an inlet and an outlet;
a carrier gas feed;
a first separating device having a downstream first detector;
a second separating device having a downstream second detector,
a first, second and third gas outlet; and
a multiport valve unit comprising a first valve, a second valve, a third valve, a fourth valve and a fifth valve in a first series circuit, a sixth valve and a seventh valve in a second series circuit and an eighth valve, a ninth valve and a tenth valve in a third series circuit wherein the sample feed is attached to a start and the sample vent is attached to an end of the first series circuit;

wherein the inlet of the metering chamber is attached to a connection between the first and second valve and the outlet of the metering chamber is attached to a connection between the fourth and fifth valve;

wherein the carrier gas feed is attached to a connection between the second and third valve and to a start of the third series circuit;

wherein an end of the third series circuit is connected to the second gas outlet;

wherein a start of the second series circuit is attached to a connection between the third and fourth valve and an end of the second series circuit is connected to the third gas outlet;

wherein the first separating device having the first detector is arranged between a connection between the sixth and seventh valve and a connection between the ninth and tenth valve; and wherein the second separating device having the second detector is arranged between a connection between the eighth and ninth valve and the first gas outlet; and wherein the first valve, the second valve, the third valve, the fourth valve, the fifth valve, the sixth valve, the seventh valve, the eighth valve, the ninth valve and the tenth valve each comprise:
a lower part formed as a disk, a recess being formed in an outer surface for each valve of the plurality of valves, into which control air is introducible via an individual control line;
a diaphragm, which on one side abuts the outer surface of the lower part containing a respective recesses;

a control disk, which abuts another side of the diaphragm; and a pairs of holes in areas opposite the each of the respective recesses, each pair of holes forming fluid ports in each valve of the plurality of valves;

grooves on its side facing away from the diaphragm, which one of (i) connect the fluid ports of valves of the plurality of valves connected in series to each other and (ii) lead from selected fluid ports to prescribed locations;

an upper part formed as a disk, which immediately or with interposition of a sealing foil, abuts a side of the control disk containing the grooves; and external ports, which are mounted on outer surfaces of at least one of (i) the upper part and (ii) the lower part facing away from the diaphragm and which are connected to the grooves and via these to the fluid ports via drilled holes leading to the prescribed locations and extending vertically to the outer surfaces.

* * * * *